(12) United States Patent
Sørensen et al.

(10) Patent No.: US 7,960,561 B2
(45) Date of Patent: Jun. 14, 2011

(54) 2-(PHENYLAMINO) BENZIMIDAZOLE DERIVATIVES AND THEIR USE AS MODULATORS OF SMALL-CONDUCTANCE CALCIUM-ACTIVATED POTASSIUM CHANNELS

(75) Inventors: Ulrik Svane Sørensen, Søborg (DK); Lene Teuber, Væløse (DK); Dan Peters, Malmö (DK); Dorte Strøbæk, Farum (DK); Tina Holm Johansen, Smørum (DK); Karin Sandager Nielsen, Fredensborg (DK); Palle Christophersen, Ballerup (DK)

(73) Assignee: Neurosearch A/S, Ballerup (DK)

( * ) Notice: Subject to any disclaimer, the term of this patent is extended or adjusted under 35 U.S.C. 154(b) by 659 days.

(21) Appl. No.: 11/919,708

(22) PCT Filed: Jun. 21, 2006

(86) PCT No.: PCT/EP2006/063405
§ 371 (c)(1),
(2), (4) Date: Oct. 31, 2007

(87) PCT Pub. No.: WO2006/136580
PCT Pub. Date: Dec. 28, 2006

(65) Prior Publication Data
US 2009/0076106 A1 Mar. 19, 2009

(30) Foreign Application Priority Data
Jun. 21, 2005 (DK) .................................. 2005 00910

(51) Int. Cl.
*A61K 31/4184* (2006.01)
*C07D 235/30* (2006.01)
(52) U.S. Cl. ..................................... 548/307.4; 514/388
(58) Field of Classification Search ................ 548/307.4
See application file for complete search history.

(56) References Cited

U.S. PATENT DOCUMENTS

| | | | |
|---|---|---|---|
| 6,518,291 B1 * | 2/2003 | Saunders et al. | 514/367 |
| 7,228,001 B2 | 6/2007 | Kobayashi et al. | |
| 2002/0132842 A1 * | 9/2002 | Hofmeister et al. | 514/395 |
| 2005/0054705 A1 | 3/2005 | Heinelt et al. | |

FOREIGN PATENT DOCUMENTS

| | | | |
|---|---|---|---|
| CA | 2430412 A1 * | 6/2002 | |
| FR | 1.358.741 A2 | 4/1964 | |
| GB | 1171904 A2 | 11/1969 | |
| JP | 2-306916 A | 12/1990 | |
| WO | WO-01/21160 A2 | 3/2001 | |
| WO | WO-02/46169 A1 | 6/2002 | |
| WO | WO-2004/069811 A1 | 8/2004 | |
| WO | WO-2004/098494 A2 | 11/2004 | |
| WO | WO-2005/044793 A2 | 5/2005 | |

OTHER PUBLICATIONS

Sailer et al., "Comparative immunohistochemical distribution of three small-conductance Ca2±activated potassium channel subunits, SK1, SK2, and SK3 in mouse brain," Mol. Cell. Neurosci., 2004, vol. 26, pp. 458-469.

Liegeois et al., "Modulation of small conductance calcium-activated potassium (SK) channels: a new challenge in medicinal chemistry," Current Medicinal Chemistry, 2003, vol. 10, pp. 625-647.

Zhu et al., "Studies on fluorine-containing aromatic heterocyclic compounds. 4. Reactions of 3-trifluoromethylphenyl and 2-chloro-5-trifluoromethylphenyl isocyanide dichlorides with bifunctional nucleophiles," Journal of Fluorine Chemistry, 1989, vol. 43, No. 3, pp. 319-327.

Caplus Accession No. 2003:959005, Alagarsamy et al., "Antibacterial activity of some 2-(substituted amino) benzinidazoles," Indian Pharmacist, 2003, vol. 2, No. 8, pp. 78-79.

Grimmett, "Product class 4: benzimidazoles," Science of Synthesis, 2002, vol. 12, pp. 529-612.

Claramunt et al., "Aromatic systems with 10 .pi. electrons derived from 3a-azapentalene. XV. Heterocyclic derivatives from 3a-azapentalene by aryne synthesis," Anales de Quimica, 1975, vol. 71, No. 2, pp. 206-207.

Murphy, "Carbonimidoyl dihalides as organic intermediates. I. The preparation of 2-aryl aminobenzimidazoles," Journal of Organic Chemistry, 1964, vol. 29, No. 6, pp. 1613-1615.

Caplus Accession No. 1954:5037, Matsui et al., "Mothproofing agents for wool. XIII. Relation between teh chemical constitution of mothproofing agents and their effects on wool," J. Soc. Org. Synthetic Chem., 1952, vol. 10, pp. 333-335.

Garin et al., "A facile synthesis of dimethyl N-aryldithiocarbonimidates and 2-arylaminobenzimidazoles," Synthesis, 1983, pp. 375-376.

Tuncbilek et al., "Synthesis and antimicrobial activity of some new anilinobenzimidazoles," Arch. Pharm. Pharm. Med. Chem., 1997, vol. 330, No. 12, pp. 372-376.

Caplus Accession No. 2001:732016, Krchnak et al., "Solid-phase traceless synthesis of selected nitrogen-containing heterocyclic compounds. The encore technique for directed sorting of modular solid support," Vollection of Czechoslovak Chemical Communications, 2001, vol. 66, No. 7, pp. 1078-1106.

Omelka et al., "EPR study of nitroxyl radicals of substituted 5-anilinotriazoles, 5-anilinotetrazoles, and 2-anilinobenzimidazoles," Collection of Czechoslovak Chemical Communications, 1992, vol. 57, No. 5, pp. 1065-1071.

Merchan et al., "Synthesis of 2-aryliminoimidazolidines and 2-arylaminobenzimidazoles from methyl n-aryldithiocarbamates," Synthesis, 1982, pp. 482-484.

Omar et al., "The cyclodesulfurization of thio compounds; XVI. Dicyclohexylbarbodiimide as an efficient cyclodesulfurizing agent in the synthesis of heterocyclic compounds from various thio compounds," Synthesis, 1977, pp. 864-865.

Krchnak et al., "A solid phase traceless synthesis of 2-arylaminobenzimidazoles," Tetrahedron Letters, 2001, vol. 42, pp. 1627-1630.

(Continued)

*Primary Examiner* — Laura L. Stockton
(74) *Attorney, Agent, or Firm* — Birch, Stewart, Kolasch & Birch, LLP

(57) ABSTRACT

This invention relates to novel 2-(phenylamino)benzimidazole derivatives useful as modulators of small-conductance calcium-activated potassium channels (SK channels).
In other aspects the invention relates to the use of these compounds in a method for therapy and to pharmaceutical compositions comprising the compounds of the invention.

6 Claims, No Drawings

OTHER PUBLICATIONS

Jarrott et al., "Characterization of .alpha.-adrenoceptors in rat and guinea pig tissues using radiolabeled agonists and antagonists," Circulation Research, 1980, vol. 46, No. 1, pp. 15-20.

Caplus Accession No. 1975:541756, Lebedeva et al., "Dependence of acute toxicity on structure in a series of 2-substituted benzimidzazoles," Meditsinskaya Parazitologiya i Parazitarnye Bolezni, 1975, vol. 44, No. 3, pp. 316-322.

Jen et al., "Amidines and related compounds. 6. Studies on structure-activity relationships of antihypertensive and antisecretory agents related to clonidine," Journal of Medicinal Chemistry, 1975, vol. 18, No. 1, pp. 90-99.

Caplus Accession No. 1990:178787, Kolesnikova et al., "Reaction of N-pentafluorophenylcarbonimidoyl dichloride with primary aminds," Zhurnal Organischeskoi Khimii, 1989, vol. 25, No. 8, pp. 1689-1695.

Wang et al., "A practical synthesis of 2-(N-substituted)-amino-benzimidazoles utilizing CuCl-promoted intramolecular cyclization of N-(2-aminoaryl)thioureas," Tetrahedron Letters, 2004, vol. 45, pp. 7167-7170.

* cited by examiner

2-(PHENYLAMINO) BENZIMIDAZOLE DERIVATIVES AND THEIR USE AS MODULATORS OF SMALL-CONDUCTANCE CALCIUM-ACTIVATED POTASSIUM CHANNELS

TECHNICAL FIELD

This invention relates to novel 2-(phenylamino)benzimidazole derivatives useful as modulators of small-conductance calcium-activated potassium channels (SK channels).

In other aspects the invention relates to the use of these compounds in a method for therapy and to pharmaceutical compositions comprising the compounds of the invention.

BACKGROUND ART

Three subtypes of small-conductance calcium-activated potassium channels (SK channels) have been cloned: SK1, SK2 and SK3 (corresponding to KCNN1-3 using the genomic nomenclature). The activity of these channels is determined by the concentration of free intracellular calcium ($[Ca^{2+}]_i$) via calmodulin that is constitutively bound to the channels. SK channels are tightly regulated by $[Ca^{2+}]_i$ in the physiological range being closed at $[Ca^{2+}]_i$ up to around 0.1 µM but fully activated at a $[Ca^{2+}]_i$ of 1 µM. Being selective for potassium, open or active SK channels have a hyperpolarizing influence on the membrane potential of the cell. SK channels are widely expressed in the central nervous system. The distribution of SK1 and SK2 show a high degree of overlap and display the highest levels of expression in neocortical, limbic and hippocampal areas in the mouse brain. In contrast, the SK3 channels show high levels of expression in the basal ganglia, thalamus and the brain stem monoaminergic neurons e.g. dorsal raphe, locus coeruleus and the ventral tegmental area (see Sailer et al.: Comparative immunohistochemical distribution of three small-conductance $Ca^{2+}$-activated potassium channel subunits, SK1, SK2, and SK3 in mouse brain; *Mol. Cell. Neurosci.* 2004 26 458-469). The SK channels are also present in several peripheral cells including skeletal muscle, gland cells, liver cells and T-lymphocytes.

The hyperpolarizing action of active SK channels plays an important role in the control of firing pattern and excitability of excitable cells. SK channel inhibitors such as apamin and bicuculline-methobromide have been demonstrated to increase excitability whereas the opener 1-EBIO is able to reduce electrical activity. In non-excitable cells where the amount of $Ca^{2+}$ influx via voltage-independent pathways is highly sensitive to the membrane potential an activation of SK channels will increase the driving force whereas a blocker of SK channels will have a depolarising effect and thus diminish the driving force for calcium.

Based on the important role of SK channels in linking $[Ca^{2+}]_i$ and membrane potential, SK channels are an interesting target for developing novel therapeutic agents.

A review of SK channels and SK channel modulators may be found in Liegeois J-F et al.: Modulation of small conductance calcium-activated potassium (SK) channels: a new challenge in medicinal chemistry"; *Current Medicinal Chemistry* 2003 10 625-647.

Known modulators of SK channels suffer from being large molecules or peptides (apamin, scyllatoxin, tubocurarine, dequalinium chloride, UCL1684) or having low potency (1-EBIO, riluzole). Thus, there is a continued need for compounds with an optimized pharmacological profile. In particular, there is a great need for selective ligands, such as SK3 channel modulators.

SUMMARY OF THE INVENTION

In its first aspect, the invention provides a compound of Formula I:

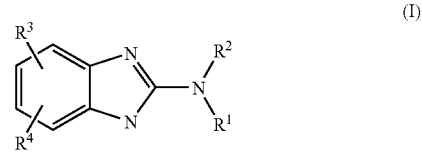

any of its isomers or any mixture of its isomers, or a pharmaceutically acceptable salt thereof, wherein $R^1$, $R^2$, $R^3$ and $R^4$ are as defined below.

In its second aspect, the invention provides a pharmaceutical composition, comprising a therapeutically effective amount of a compound of the invention, any of its isomers or any mixture of its isomers, or a pharmaceutically acceptable salt thereof, together with at least one pharmaceutically acceptable carrier, excipient or diluent.

In a further aspect, the invention provides the use of a compound of the invention, any of its isomers or any mixture of its isomers, or a pharmaceutically acceptable salt thereof, for the manufacture of a pharmaceutical composition for the treatment, prevention or alleviation of a disease or a disorder or a condition of a mammal, including a human, which disease, disorder or condition is responsive to modulation of SK channels.

In a still further aspect, the invention relates to a method for treatment, prevention or alleviation of a disease or a disorder or a condition of a living animal body, including a human, which disorder, disease or condition is responsive to modulation of SK channels, which method comprises the step of administering to such a living animal body in need thereof a therapeutically effective amount of a compound of the invention, any of its isomers or any mixture of its isomers, or a pharmaceutically acceptable salt thereof.

Other objects of the invention will be apparent to the person skilled in the art from the following detailed description and examples.

DETAILED DISCLOSURE OF THE INVENTION

2-(phenylamino)benzimidazole Derivatives

In its first aspect the present invention provides a compound of Formula I:

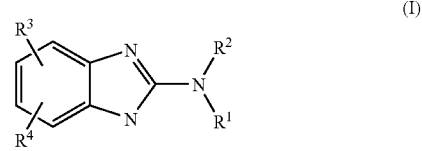

any of its isomers or any mixture of its isomers, or a pharmaceutically acceptable salt thereof, wherein $R^1$ represents a phenyl group;

which phenyl group is substituted with one or more substituents independently selected from the group consisting of:
halo, trifluoromethyl, trifluoromethoxy, cyano, alkyl, alkoxy and phenyl;

$R^2$ represents hydrogen or alkyl;

$R^3$ and $R^4$ independent of each other are selected from the group consisting of:
hydrogen, halo, trifluoromethyl, trifluoromethoxy, cyano, —NR'R", alkyl and alkoxy wherein R' and R" independent of each other are hydrogen or alkyl;

with the proviso that the compound is not N-Benzimidazol-2-yl)-aniline, N-Benzimidazol-2-yl)-4-chloroaniline, N-Benzimidazol-2-yl)-4-fluoroaniline, N-Benzimidazol-2-yl)-3-chloro-aniline, N-Benzimidazol-2-yl)-3-trifluoromethyl-aniline, or N-Benzimidazol-2-yl)-4-chloro-3-trifluoromethyl-aniline.

In one embodiment, $R^1$ represents

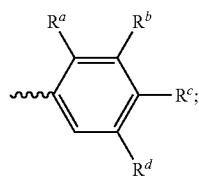

wherein $R^a$, $R^b$, $R^c$ and $R^d$ independent of each other are selected from the group consisting of:
hydrogen, halo, trifluoromethyl, trifluoromethoxy, cyano, alkyl, alkoxy and phenyl; with the proviso that not all four of $R^a$, $R^b$, $R^c$ and $R^d$ represent hydrogen.

In a more preferred embodiment $R^a$, $R^b$, $R^c$ and $R^d$ independent of each other are selected from the group consisting of hydrogen, halo, trifluoromethyl, trifluoromethoxy, cyano and alkyl; with the proviso that not all four of $R^a$, $R^b$, $R^c$ and $R^d$ represent hydrogen.

In a second embodiment, $R^a$ and $R^b$ independent of each other are selected from the group consisting of: halo, trifluoromethyl, trifluoromethoxy, cyano, alkyl, alkoxy and phenyl; and $R^c$ and $R^d$ represent hydrogen. In a special embodiment, $R^a$ represents alkyl, such as methyl, and $R^b$ represents trifluoromethyl. In a further embodiment, $R^a$ represents halo, such as fluoro, and $R^b$ represents trifluoromethyl.

In a more preferred embodiment, $R^a$ and $R^b$ independent of each other are selected from the group consisting of halo, trifluoromethyl, trifluoromethoxy, cyano, and alkyl; and $R^c$ and $R^d$ represent hydrogen.

In a further embodiment, $R^b$ and $R^c$ independent of each other are selected from the group consisting of: halo, trifluoromethyl, trifluoromethoxy, cyano, alkyl, alkoxy and phenyl; and $R^a$ and $R^d$ represent hydrogen. In a special embodiment, $R^b$ represents halo, such as chloro or fluoro, and $R^c$ represents halo, such as chloro or fluoro. In a further embodiment, $R^b$ represents trifluoromethyl and $R^c$ represents halo, such as chloro, fluoro or bromo. In a still further embodiment, $R^b$ represents alkyl, such as methyl, and $R^c$ represents halo, such as fluoro. In a further embodiment, $R^b$ represents trifluoromethyl and $R^c$ represents alkyl, such as methyl.

In a more preferred embodiment, $R^b$ and $R^c$ independent of each other are selected from the group consisting of halo, trifluoromethyl, trifluoromethoxy, cyano and alkyl; and $R^a$ and $R^d$ represent hydrogen.

In a still further embodiment, $R^b$ and $R^d$ independent of each other are selected from the group consisting of: halo, trifluoromethyl, trifluoromethoxy, cyano, alkyl, alkoxy and phenyl; and $R^a$ and $R^c$ represent hydrogen. In a special embodiment, $R^b$ represents halo, such as chloro or fluoro, and $R^d$ represents halo, such as chloro or fluoro. In a further embodiment, $R^b$ represents trifluoromethyl and $R^d$ represents trifluoromethyl. In a still further embodiment, $R^b$ represents trifluoromethyl and $R^d$ represents halo, such as fluoro.

In a more preferred embodiment, $R^b$ and $R^d$ independent of each other are selected from the group consisting of halo, trifluoromethyl, trifluoromethoxy, cyano and alkyl; and $R^a$ and $R^c$ represent hydrogen.

In a further embodiment, $R^a$, $R^b$ and $R^c$ independent of each other are selected from the group consisting of: halo, trifluoromethyl, trifluoromethoxy, cyano, alkyl, alkoxy and phenyl; and $R^d$ represents hydrogen. In a special embodiment, $R^a$ represents halo, such as fluoro, $R^b$ represents halo, such as fluoro, and $R^c$ represents halo, such as fluoro.

In a more preferred embodiment, $R^a$, $R^b$ and $R^c$ independent of each other are selected from the group consisting of halo, trifluoromethyl, trifluoromethoxy, cyano and alkyl; and $R^d$ represents hydrogen.

In a still further embodiment, one of $R^a$, $R^b$ and $R^c$ is selected from the group consisting of: halo, trifluoromethyl, trifluoromethoxy, cyano, alkyl, alkoxy and phenyl; and $R^d$ and the remaining two of $R^a$, $R^b$ and $R^c$ represent hydrogen. In a special embodiment, $R^c$ represents halo, such as chloro or fluoro. In a further embodiment, $R^c$ represents trifluoromethyl. In a still further embodiment, $R^c$ represents trifluoromethoxy. In a further embodiment, $R^b$ represents halo, such as chloro. In a still further embodiment, $R^b$ represents trifluoromethyl.

In a more preferred embodiment, one of $R^a$, $R^b$ and $R^c$ is selected from the group consisting of halo, trifluoromethyl, trifluoromethoxy, cyano and alkyl; and $R^d$ and the remaining two of $R^a$, $R^b$ and $R^c$ represent hydrogen.

In a further embodiment, $R^2$ represents hydrogen.

In a still further embodiment, $R^2$ represents alkyl, such as methyl.

In a further embodiment, $R^3$ and $R^4$ represent hydrogen.

In a special embodiment the chemical compound of the invention is
N-(Benzimidazol-2-yl)-4-chloroaniline;
N-(Benzimidazol-2-yl)-4-chloro-3-(trifluoromethyl)aniline;
N-(Benzimidazol-2-yl)-3,4-dichloroaniline;
N-(Benzimidazol-2-yl)-4-(trifluoromethyl)aniline;
N-(Benzimidazol-2-yl)-3-chloroaniline;
N-(Benzimidazol-2-yl)-4-(trifluoromethoxy)aniline;
N-(Benzimidazol-2-yl)-4-fluoroaniline;
N-(Benzimidazol-2-yl)-3,4-difluoroaniline;
N-(Benzimidazol-2-yl)-3,5-difluoroaniline;
N-(Benzimidazol-2-yl)-3-(trifluoromethyl)aniline;
N-(Benzimidazol-2-yl)-4-fluoro-3-(trifluoromethyl)aniline;
N-(Benzimidazol-2-yl)-4-fluoro-3-methylaniline;
N-(Benzimidazol-2-yl)-3,5-bis(trifluoromethyl)aniline;
N-(Benzimidazol-2-yl)-3-chloro-4-fluoroaniline;
N-(Benzimidazol-2-yl)-3,5-dichloroaniline;
N-(Benzimidazol-2-yl)-4-bromo-3-(trifluoromethyl)aniline;
N-(Benzimidazol-2-yl)-4-methyl-3-(trifluoromethyl) aniline;
N-(Benzimidazol-2-yl)-3-fluoro-5-(trifluoromethyl)aniline;
N-(Benzimidazol-2-yl)-2-methyl-3-(trifluoromethyl) aniline;
N-(Benzimidazol-2-yl)-2-fluoro-3-(trifluoromethyl)aniline;
N-(Benzoimidazol-2-yl)-2,3,4-trifluoroaniline;
N-(Benzoimidazol-2-yl)-N-methyl-3,4-dichloroaniline;
N-(Benzoimidazol-2-yl)-3-cyano-aniline;
N-(Benzoimidazol-2-yl)-3-methoxy-5-(trifluoromethyl) aniline;

N-(Benzoimidazol-2-yl)-4-isopropyl-aniline;
N-(Benzoimidazol-2-yl)-2-chloro-5-(trifluoromethyl) aniline;
N-(Benzoimidazol-2-yl)-2-methyl-5-(trifluoromethyl) aniline; or
N-(Benzoimidazol-2-yl)-2-phenyl-aniline;
or a pharmaceutically acceptable salt thereof.

Any combination of two or more of the embodiments as described above is considered within the scope of the present invention.

Definition of Substituents

In the context of this invention halo represents fluoro, chloro, bromo or iodo.

In the context of this invention an alkyl group designates a univalent saturated, straight or branched hydrocarbon chain. The hydrocarbon chain preferably contains of from one to six carbon atoms ($C_{1-6}$-alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

Alkoxy is O-alkyl, wherein alkyl is as defined above.

Pharmaceutically Acceptable Salts

The chemical compound of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate derived, the phthalate, the salicylate, the sorbate, the stearate, the succinate, the tartrate, the toluene-p-sulphonate, and the like. Such salts may be formed by procedures well known and described in the art.

Examples of pharmaceutically acceptable cationic salts of a chemical compound of the invention include, without limitation, the sodium, the potassium, the calcium, the magnesium, the zinc, the aluminium, the lithium, the choline, the lysine, and the ammonium salt, and the like, of a chemical compound of the invention containing an anionic group. Such cationic salts may be formed by procedures well known and described in the art.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Examples of pre- or prodrug forms of the chemical compound of the invention include examples of suitable prodrugs of the substances according to the invention include compounds modified at one or more reactive or derivatizable groups of the parent compound. Of particular interest are compounds modified at a carboxyl group, a hydroxyl group, or an amino group. Examples of suitable derivatives are esters or amides.

The chemical compound of the invention may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Steric Isomers

It will be appreciated by those skilled in the art that the compounds of the present invention may contain one or more chiral centers, and that such compounds exist in the form of isomers.

Moreover, the chemical compounds of the present invention may exist as enantiomers in (+) and (−) forms as well as in racemic forms (±). The racemates of these isomers and the individual isomers themselves are within the scope of the present invention.

The invention includes all such isomers and any mixtures thereof including racemic mixtures.

Racemic forms can be resolved into the optical antipodes by known methods and techniques. One way of separating the isomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l-(tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Optical active compounds can also be prepared from optical active starting materials.

Labelled Compounds

The compounds of the invention may be used in their labelled or unlabelled form. In the context of this invention the labelled compound has one or more atoms replaced by an atom having an atomic mass or mass number different from the atomic mass or mass number usually found in nature. The labelling will allow easy quantitative detection of said compound.

The labelled compounds of the invention may be useful as diagnostic tools, radio tracers, or monitoring agents in various diagnostic methods, and for in vivo receptor imaging.

The labelled isomer of the invention preferably contains at least one radio-nuclide as a label. Positron emitting radionuclides are all candidates for usage. In the context of this invention the radionuclide is preferably selected from $^{2}H$ (deuterium), $^{3}H$ (tritium), $^{13}C$, $^{14}C$, $^{131}I$, $^{125}I$, $^{123}I$, and $^{18}F$.

The physical method for detecting the labelled isomer of the present invention may be selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Methods of Preparation

The chemical compounds of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

Compounds of the invention may be tested for their ability to modulate SK channels in vitro. Functional modulation can be determined by measuring the compound-induced change in SK current by the patch clamp technique as described by Strøbæk et al.: Pharmacological characterization of small-conductance $Ca^{2+}$-activated K channels expressed in HEK293 cells; *British Journal of Pharmacology* 2000 129 991-999. From this type of measurements the potency of a given compound can be determined as e.g. $K_i$ or $IC_{50}$ values for blockers/inhibitors and $EC_{50}$ values for openers/activators. Similar data can be obtained from other patch clamp configurations and from channels expressed endogenously in various cell lines.

In one embodiment, the compounds of the invention show selectivity for SK3 over SK1 and SK2. In a further embodiment, the compounds of the invention are positive SK channel modulators, such as positive SK3 channel modulators. In a still further embodiment, the compounds of the invention are negative modulators, such as negative SK3 channel modulators. In a special embodiment, the compounds of the invention are SK channel blockers, such as SK3 channel blockers.

Based on the activity observed in the patch clamp experiments, the compound of the invention is considered useful for the treatment, prevention or alleviation of a disease or a disorder or a condition of a mammal, including a human, which disease, disorder or condition is responsive to modulation of SK channels.

In a special embodiment, the compounds of the invention are considered useful for the treatment, prevention or alleviation of: absence seizures, agerelated memory loss, Alzheimer's disease, angina pectoris, arrhythmia, asthma, anxiety, ataxia, attention deficits, baldness, bipolar disorder, bladder hyperexcitability, bladder outflow obstruction, bladder spasms, brain tumors, cerebral ischaemia, chronic obstructive pulmonary disease, cancer, cardiovascular disorders, cognitive dysfunction, colitis, constipation, convulsions, coronary artery spasms, coronary hearth disease, cystic fibrosis, dementia, depression, diabetes type II, dysmenorrhoea, epilepsy, gastrointestinal dysfunction, gastroesophageal reflux disorder, gastrointestinal hypomotility disorders gastrointestinal motility insufficiency, hearing loss, hyperinsulinemia, hypertension, immune suppression, inflammatory bowel disease, inflammatory pain, intermittent claudication, irritable bowel syndrome, ischaemia, ischaemic hearth disease, learning deficiencies, male erectile dysfunction, manic depression, memory deficits, migraine, mood disorders, motor neuron diseases, myokymia, myotonic dystrophy, myotonic muscle dystrophia, narcolepsy, neuropathic pain, pain, Parkinson's disease, polycystic kidney disease, postoperative ileus, premature labour, psychosis, psychotic disorders, renal disorders, Reynaud's disease, rhinorrhoea, secretory diarrhoea, seizures, Sjorgren's syndrome, sleep apnea, spasticity, sleeping disorders, stroke, traumatic brain injury, trigeminal neuralgia, urinary incontinence, urinogenital disorders, vascular spasms, vision loss, and xerostomia.

It is at present contemplated that a suitable dosage of the active pharmaceutical ingredient (API) is within the range of from about 0.1 to about 1000 mg API per day, more preferred of from about 10 to about 500 mg API per day, most preferred of from about 30 to about 100 mg API per day, dependent, however, upon the exact mode of administration, the form in which it is administered, the indication considered, the subject and in particular the body weight of the subject involved, and further the preference and experience of the physician or veterinarian in charge.

Preferred compounds of the invention show a biological activity in the sub-micromolar and micromolar range, i.e. of from below 1 to about 100 µM.

Pharmaceutical Compositions

In another aspect the invention provides novel pharmaceutical compositions comprising a therapeutically effective amount of the chemical compound of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the chemical compound of the invention, or a pharmaceutically acceptable salt or derivative thereof, together with one or more pharmaceutically acceptable carriers, and, optionally, other therapeutic and/or prophylactic ingredients, known and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition of the invention can be prepared by any skilled person by use of standard methods and conventional techniques appropriate to the desired formulation. When desired, compositions adapted to give sustained release of the active ingredient may be employed.

Further details on techniques for formulation and administration may be found in the latest edition of *Remington's Pharmaceutical Sciences* (Maack Publishing Co., Easton, Pa.).

The actual dosage depend on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Methods of Therapy

In another aspect the invention provides a method for the treatment, prevention or alleviation of a disease or a disorder or a condition of a living animal body, including a human, which disease, disorder or condition is responsive to modulation of SK channels, and which method comprises administering to such a living animal body, including a human, in need thereof an effective amount of a chemical compound of the invention.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

EXAMPLES

The invention is further illustrated with reference to the following examples, which are not intended to be in any way limiting to the scope of the invention as claimed.
General: The procedures represent generic procedures used to prepare compounds of the invention. Abbreviations used are as follows:
Me: methyl
mp: melting point
MW: microwave
rt: room temperature
Procedure A 2-Chlorobenzimidazole and the required amine were suspended in acetonitrile in a closed vial and heated to 150-200° C. for 15-45 min by use of microwave (MW) irradiation. After cooling to rt the precipitated solid was filtered off and washed with acetonitrile to give the desired product as a HCl salt. Alternatively, the precipitate was filtered off and recrystallised from a mixture of $CH_3CN$/MeOH or purified by column chromatography or preparative LCMS to give the desired product as the free base.

An example of Procedure A, the preparation of N-(benzimidazol-2-yl)-4-chloro-3-(trifluoromethyl)aniline, is shown in Scheme 1.

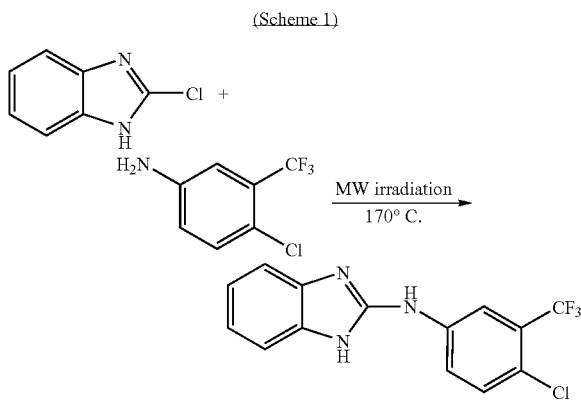

(Scheme 1)

Example 1

N-(Benzimidazol-2-yl)-4-chloroaniline

The title compound was prepared from 2-chlorobenzimidazole and 4-chloroaniline by Procedure A. The product was isolated by filtration and recrystallisation to give the title compound as a hydrochloride salt (white solid, mp 238-240° C.). MS(ES$^+$) m/z 244 ([M+1]$^+$, 100).

Example 2

N-(Benzimidazol-2-yl)-4-chloro-3-(trifluoromethyl)aniline

The title compound was prepared from 2-chlorobenzimidazole and 4-chloro-3-(trifluoromethyl)aniline by Procedure A. The product was isolated by filtration and recrystallisation to give the title compound as a hydrochloride salt (white solid, mp 255-260° C.). MS(ES$^+$) m/z 312 ([M+1]$^+$, 100).

Example 3

N-(Benzimidazol-2-yl)-3,4-dichloroaniline

The title compound was prepared from 2-chlorobenzimidazole and 3,4-dichloroaniline by Procedure A. The product was isolated by filtration to give the title compound as a hydrochloride salt (white solid, mp>270° C.). MS(ES$^+$) m/z 278 (M$^+$, 100).

Example 4

N-(Benzimidazol-2-yl)-4-(trifluoromethyl)aniline

The title compound was prepared from 2-chlorobenzimidazole and 4-(trifluoromethyl)aniline by Procedure A. The product was isolated by filtration and preparative LCMS to give the title compound as the free base (white solid, mp 199-200° C.). MS(ES$^+$) m/z 278 ([M+1]$^+$, 100).

Example 5

N-(Benzimidazol-2-yl)-3-chloroaniline

The title compound was prepared from 2-chlorobenzimidazole and 3-chloroaniline by Procedure A. The product was isolated by filtration to give the title compound as a hydrochloride salt (white solid, mp 252-257° C.). MS(ES$^+$) m/z 244 ([M+1]$^+$, 100).

Example 6

N-(Benzimidazol-2-yl)-4-(trifluoromethoxy)aniline

The title compound was prepared from 2-chlorobenzimidazole and 4-(trifluoromethoxy)aniline by Procedure A. The product was isolated by filtration to give the title compound as a hydrochloride salt (white solid, mp 250-251° C.). MS(ES$^+$) m/z 294 ([M+1]$^+$, 100).

Example 7

N-(Benzimidazol-2-yl)-4-fluoroaniline

The title compound was prepared from 2-chlorobenzimidazole and 4-fluoroaniline by Procedure A. The product was isolated by filtration to give the title compound as a hydrochloride salt (solid, mp 215-216° C.). MS(ES$^+$) m/z 228 ([M+1]$^+$, 100).

Example 8

N-(Benzimidazol-2-yl)-3,4-difluoroaniline

The title compound was prepared from 2-chlorobenzimidazole and 3,4-difluoroaniline by Procedure A. The product was isolated by filtration to give the title compound as a hydrochloride salt (white solid, mp 283-284° C.). MS(ES$^+$) m/z 246 ([M+1]$^+$, 100).

Example 9

N-(Benzimidazol-2-yl)-3,5-difluoroaniline

The title compound was prepared from 2-chlorobenzimidazole and 3,5-difluoroaniline by Procedure A. The product was isolated by filtration to give the title compound as a hydrochloride salt (white solid, mp 292-293° C.). MS(ES$^+$) m/z 246 ([M+1]$^+$, 100).

Example 10

N-(Benzimidazol-2-yl)-3-(trifluoromethyl)aniline

The title compound was prepared from 2-chlorobenzimidazole and 3-(trifluoromethyl)aniline by Procedure A. The product was isolated by filtration and preparative LCMS to give the title compound as the free base (white solid, mp 160-162° C.). MS(ES$^+$) m/z 278 ([M+1]$^+$, 100).

Example 11

N-(Benzimidazol-2-yl)-4-fluoro-3-(trifluoromethyl)aniline

The title compound was prepared from 2-chlorobenzimidazole and 4-fluoro-3-(trifluoromethyl)aniline by Procedure A. The product was isolated by filtration to give the title compound as a hydrochloride salt (white solid, mp 255-257° C.). MS(ES$^+$) m/z 296 ([M+1]$^+$, 100).

Example 12

N-(Benzimidazol-2-yl)-4-fluoro-3-methylaniline

The title compound was prepared from 2-chlorobenzimidazole and 4-fluoro-3-methylaniline by Procedure A. The product was isolated by filtration to give the title compound as a hydrochloride salt (solid, mp 246-248° C.). MS(ES$^+$) m/z 242 ([M+1]$^+$, 100).

Example 13

N-(Benzimidazol-2-yl)-3,5-bis(trifluoromethyl)aniline

The title compound was prepared from 2-chlorobenzimidazole and 3,5-bis(trifluoromethyl)aniline by Procedure A. The product was isolated by filtration to give the title compound as a hydrochloride salt (white solid, mp 245-246° C.). MS(ES$^+$) m/z 346 ([M+1]$^+$, 100).

Example 14

N-(Benzimidazol-2-yl)-3-chloro-4-fluoroaniline

The title compound was prepared from 2-chlorobenzimidazole and 3-chloro-4-fluoroaniline by Procedure A. The product was isolated by filtration to give the title compound as a hydrochloride salt (white solid, mp 306-307° C.). MS(ES$^+$) m/z 262 ([M+1]$^+$, 100).

Example 15

N-(Benzimidazol-2-yl)-3,5-dichloroaniline

The title compound was prepared from 2-chlorobenzimidazole and 3,5-dichloroaniline by Procedure A. The product was isolated by filtration to give the title compound as a hydrochloride salt (solid, mp 317-318° C.). MS(ES$^+$) m/z 278 (M$^+$, 100).

Example 16

N-(Benzimidazol-2-yl)-4-bromo-3-(trifluoromethyl)aniline

The title compound was prepared from 2-chlorobenzimidazole and 4-bromo-3-(trifluoromethyl)aniline by Procedure A. The product was isolated by filtration to give the title compound as a hydrochloride salt (white solid, mp 262-264° C.). MS(ES$^+$) m/z 356 (M$^+$, 100).

Example 17

N-(Benzimidazol-2-yl)-4-methyl-3-(trifluoromethyl)aniline

The title compound was prepared from 2-chlorobenzimidazole and 4-methyl-3-(trifluoromethyl)aniline by Procedure A. The product was isolated by filtration to give the title compound as a hydrochloride salt (white solid, mp>265° C.). MS(ES$^+$) m/z 292 ([M+1]$^+$, 100).

Example 18

N-(Benzimidazol-2-yl)-3-fluoro-5-(trifluoromethyl)aniline

The title compound was prepared from 2-chlorobenzimidazole and 3-fluoro-5-(trifluoromethyl)aniline by Procedure A. The product was isolated by filtration to give the title compound as a hydrochloride salt (white solid, mp 263-265° C.). MS(ES$^+$) m/z 296 ([M+1]$^+$, 100).

Example 19

N-(Benzimidazol-2-yl)-2-methyl-3-(trifluoromethyl)aniline

The title compound was prepared from 2-chlorobenzimidazole and 2-methyl-3-(trifluoromethyl)aniline by Procedure A. The product was isolated by filtration and preparative

Example 20

N-(Benzimidazol-2-yl)-2-fluoro-3-(trifluoromethyl)aniline

The title compound was prepared from 2-chlorobenzimidazole and 2-fluoro-3-(trifluoromethyl)aniline by Procedure A. The product was isolated by filtration and preparative LCMS to give the title compound as the free base (solid, mp 91-92° C.). MS(ES$^+$) m/z 296 ([M+1]$^+$, 100).

Example 21

N-(Benzimidazol-2-yl)-2,3,4-trifluoroaniline

The title compound was prepared from 2-chlorobenzimidazole and 2,3,4-trifluoroaniline by Procedure A. The product was isolated by filtration and preparative LCMS to give the title compound as the free base (white solid, mp 182-183° C.). MS(ES$^+$) m/z 264 ([M+1]$^+$, 100).

Example 22

N-(Benzoimidazol-2-yl)-N-methyl-3,4-dichloroaniline

The title compound was prepared from 2-chlorobenzimidazole and 3,4-dichhloro-N-methylaniline by Procedure A. The product was isolated by filtration to give the title compound as a hydrochloride salt (white solid, mp>275° C.). MS(ES$^+$) m/z 292 (M$^+$, 100).

Example 23

N-(Benzoimidazol-2-yl)-3-cyanoaniline

The title compound was prepared from 2-chlorobenzimidazole and 3-aminobenzonitrile by Procedure A. The product was isolated by filtration and preparative LCMS to give the title compound as the free base (white solid, mp 272-274° C.). MS(ES$^+$) m/z 235 ([M+1]$^+$, 100).

Example 24

N-(Benzoimidazol-2-yl)-3-methoxy-5-(trifluoromethyl)aniline

The title compound was prepared from 2-chlorobenzimidazole and 3-methoxy-5-(trifluoromethyl)aniline by Procedure A. The product was isolated by filtration to give the title compound as a hydrochloride salt (white solid, mp 212-213° C.). MS(ES$^+$) m/z 308 ([M+1]$^+$, 100).

Example 25

N-(Benzoimidazol-2-yl)-4-isopropylaniline

The title compound was prepared from 2-chlorobenzimidazole and 4-isopropylaniline by Procedure A. The product was isolated upon basic work-up and recrystallized from acetonitrile to give the title compound as the free base (white solid, mp 179-180° C.). MS(ES$^+$) m/z 252 ([M+1]$^+$, 100).

Example 26

N-(Benzoimidazol-2-yl)-2-chloro-5-(trifluoromethyl)aniline

The title compound was prepared from 2-chlorobenzimidazole and 3-amino-4-chlorobenzotrifluoride by Procedure A. The product was isolated upon basic work-up and purified by preparative LCMS to give the title compound as the free base. $^1$NMR (CDCl$_3$) δ 6.40 (br s, 2H), 7.11-7.15 (d, 1H), 7.18-7.25 (m, 2H), 7.35-7.41 (d, 1H), 7.42-7.46 (m, 2H), 8.57 (s, 1H). MS(ES$^+$) m/z 312 ([M+1]$^+$, 100).

Example 27

N-(Benzoimidazol-2-yl)-2-methyl-5-(trifluoromethyl)aniline

The title compound was prepared from 2-chlorobenzimidazole and 3-amino-4-methylbenzotrifluoride by Procedure A. The product was isolated upon basic work-up and purified by preparative LCMS to give the title compound as the free base. $^1$NMR (DMSO-d6) δ 2.40 (s, 3H), 6.95-7.03 (m, 2H), 7.20-7.25 (m, 1H), 7.31-7.42 (m, 3H), 8.63 (s, 1H), 8.88 (s, 1H), 10.9 (s, 1H). MS(ES$^+$) m/z 292 ([M+1]$^+$, 100).

Example 28

N-(Benzoimidazol-2-yl)-2-phenylaniline

The title compound was prepared from 2-chlorobenzimidazole and 2-amino-biphenyl by Procedure A. The crude product was purified by preparative LCMS to give the title compound as the free base (white solid, mp 152-154° C.). MS(ES$^+$) m/z 286 ([M+1]$^+$, 100).

The invention claimed is:

1. A compound of Formula I:

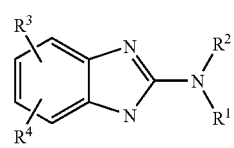

(I)

any of its stereoisomers or any mixture of its stereoisomers, or a pharmaceutically acceptable salt thereof; wherein R$^1$ represents

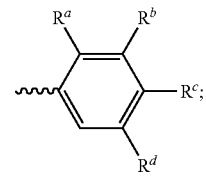

wherein either
  R$^b$ is selected from the group consisting of: trifluoromethyl and trifluoromethoxy;
  R$^c$ is selected from the group consisting of: fluoro and bromo; and
  R$^a$ and R$^d$ each represent hydrogen;
or
  R$^b$ is selected from the group consisting of: halo, trifluoromethyl and trifluoromethoxy;
  R$^d$ is selected from the group consisting of: halo, trifluoromethyl and trifluoromethoxy; and
  R$^a$ and R$^c$ each represent hydrogen;
and R$^2$, R$^3$ and R$^4$ each represent hydrogen.

2. The compound of claim 1, wherein
$R^b$ is selected from the group consisting of: trifluoromethyl and trifluoromethoxy;
$R^c$ is selected from the group consisting of: fluoro and bromo; and
$R^a$ and $R^d$ each represent hydrogen.

3. The compound of claim 1, wherein
$R^b$ is selected from the group consisting of: halo, trifluoromethyl and trifluoromethoxy;
$R^d$ is selected from the group consisting of: halo, trifluoromethyl and trifluoromethoxy; and
$R^a$ and $R^c$ each represent hydrogen.

4. The compound of claim 1 or 2, which is
N-(Benzimidazol-2-yl)-4-fluoro-3-(trifluoromethyl)aniline; or
N-(Benzimidazol-2-yl)-4-bromo-3-(trifluoromethyl)aniline;
or a pharmaceutically acceptable salt thereof.

5. The compound of claim 1 or 3, which is
N-(Benzimidazol-2-yl)-3,5-bis(trifluoromethyl)aniline;
N-(Benzimidazol-2-yl)-3,5-dichloroaniline; or
N-(Benzimidazol-2-yl)-3-fluoro-5-(trifluoromethyl)aniline;
or a pharmaceutically acceptable salt thereof.

6. A pharmaceutical composition, comprising a therapeutically effective amount of a compound of any one of claims 1-3, or any of its stereoisomers or any mixture of its stereoisomers, or a pharmaceutically acceptable salt thereof, together with at least one pharmaceutically acceptable carrier, excipient or diluent.

* * * * *